United States Patent [19]

Tamura et al.

[11] Patent Number: 5,191,074
[45] Date of Patent: Mar. 2, 1993

[54] β-LACTAM COMPOUNDS AND PRODUCTION PROCESS THEREOF

[75] Inventors: Yasumitsu Tamura, 9-24, Sakasegawa 2-chome, Takarazuka, Hyogo 665; Junichi Haruta, Hirakata; Nishi Koichi, Osaka, all of Japan

[73] Assignees: Yasumitsu Tamura; Shionogi & Co., Ltd., both of Tokyo, Japan

[21] Appl. No.: 746,083

[22] Filed: Aug. 12, 1991

Related U.S. Application Data

[60] Continuation of Ser. No. 478,469, Feb. 9, 1990, abandoned, which is a division of Ser. No. 164,062, Mar. 3, 1988, abandoned.

[30] Foreign Application Priority Data

Mar. 6, 1987 [JP] Japan .................. 62-52816

[51] Int. Cl.$^5$ ............ C07B 55/00; C07B 37/04; C07D 205/08; C07F 7/10
[52] U.S. Cl. .................................. 540/200
[58] Field of Search .................. 540/200, 350

[56] References Cited

U.S. PATENT DOCUMENTS

| 4,565,808 | 1/1986 | Andrus | 540/200 |
|---|---|---|---|
| 4,709,064 | 11/1987 | Shibasaki, II | 540/200 |
| 4,816,577 | 3/1989 | Bender | 540/200 |

FOREIGN PATENT DOCUMENTS 58-152866  9/1983  Japan .................. 540/200

OTHER PUBLICATIONS

Shibaski I Tet. Letters 23, 2875 (1982).
Yamaguchi, Chem Letters 1987, 1519-22.
Keinan, J. Org. Chem. 48, 5302-09 (1983).
Prasad, Tet. Letters 29, 4257-60 (1988).
"8th Symposium on Medicinal Chemistry" (Osaka, 1986) pp. 21-24.
Chapman, "Correlation Analysis in Chemistry-Recent Advances" pp. 461. 463.
Shih, Heterocycle 21, 29-40 (1984).

*Primary Examiner*—Mark L. Berch
*Attorney, Agent, or Firm*—Burgess, Ryan & Wayne

[57] ABSTRACT

A process for producing a β-lactam compound of the formula

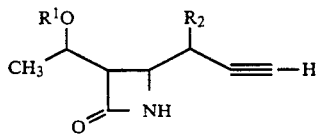

wherein $OR^1$ is a protected or unprotected hydroxyl group; $R_2$ is a $C_1$ to $C_7$ alkyl or aryl group; from an azetidinone compound of the formula

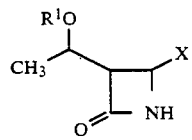

wherein X is an electronegative group removable through the reaction in three steps in which the second step subjects the β-lactam compound obtained in the first step to silylation to convert the $R^2$ group to the beta form.

4 Claims, No Drawings

β-LACTAM COMPOUNDS AND PRODUCTION PROCESS THEREOF

This application is a continuation of application Ser. No. 478,469, filed Feb. 9, 1990, which is a divisional of Ser. No. 164,062 filed Mar. 3, 1988, now abandoned.

FIELD OF THE INVENTION

This invention relates to novel β-lactam compounds, which contain a hydroxyethyl group at the 3-position, being the hydroxyl group in the hydroxyethyl group protected or unprotected, and a butynyl group at the 4-position, and also to processes for producing the compounds.

BACKGROUND OF THE INVENTION

Thienamycin (10 is produced by fungi of Actinomyces and is known to possess extremely potent antimicrobial activities. Its discovery initiated intensive research on carbapenem compounds, resulting in publication of imipenem

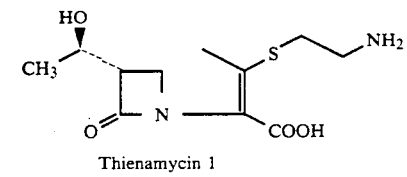

Thienamycin 1

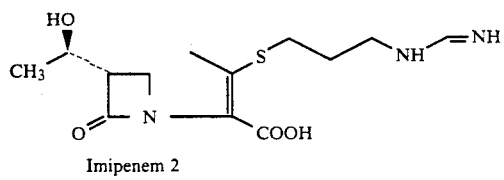

Imipenem 2

However, these carbapenem compounds are far from satisfactory in terms of chemical stability and resistance to renal dehydropeptidase-I (DHP-I). Consequently, investigation has been conducted into more stable carbapenem compounds exhibiting potent antimicrobial activity, which led in 1984 to the finding that 1β-methylcarbapenem (3) having a β-methyl group at the 1-position is stable and possesses strong antimicrobial activity.

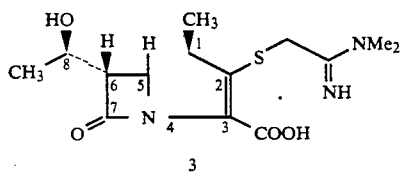

The said compound (3) contains four consecutive asymmetric carbons ($C_1$, $C_5$, $C_6$, $C_8$), and in view of the fact that most of the publications on its synthesis are concerned with the utilization of optically active azetidinone (4) as an intermediate, the synthesis of the intermediate (4) has been considered to be the key to the commercial production of the said compound (3).

According to the literature published so far on the synthesis of the compound (4), four reports dealt with the stereospecific synthesis, one report was concerned with the stereospecific reduction and one report with isomerization, as is illustrated below in the reaction formulas:

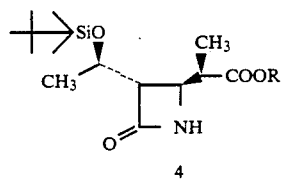

4

(Stereospecific synthesis)

1) 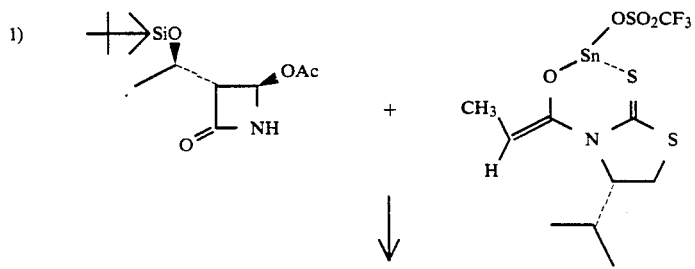

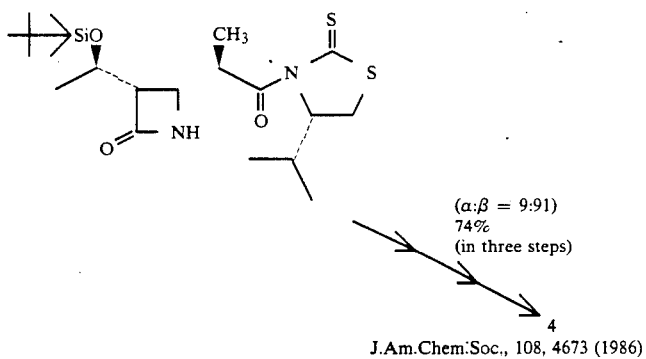
J.Am.Chem.Soc., 108, 4673 (1986)
2) 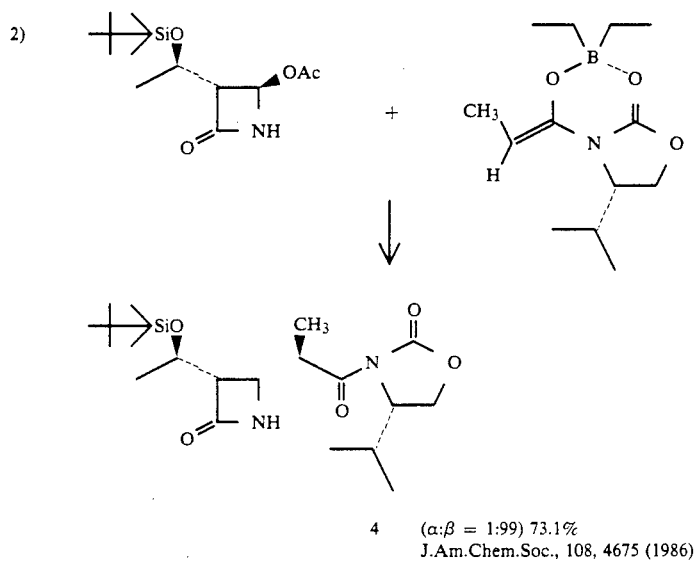
4  (α:β = 1:99) 73.1%
J.Am.Chem.Soc., 108, 4675 (1986)
3) 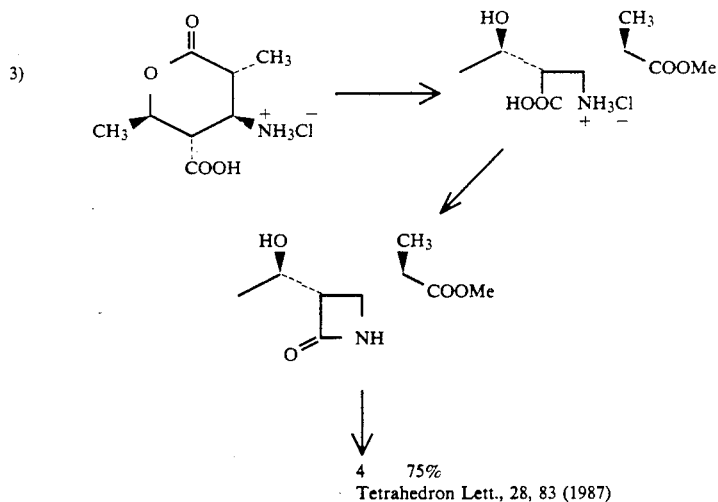
4  75%
Tetrahedron Lett., 28, 83 (1987)
4) 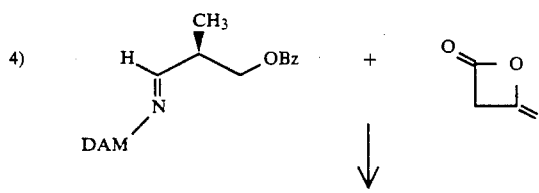

-continued

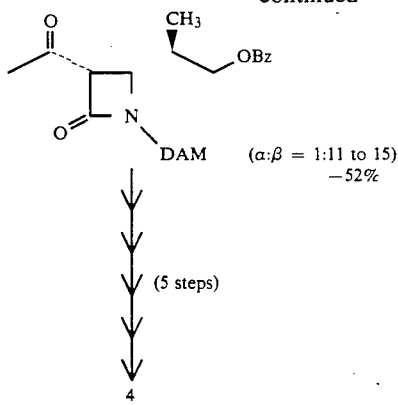

(α:β = 1:11 to 15)
−52%

↓↓↓↓↓ (5 steps)

4

The 13th Symposium of Progresses
of Reactions & Syntheses, pp.72 (1986)

(Stereospecific reduction)

5) 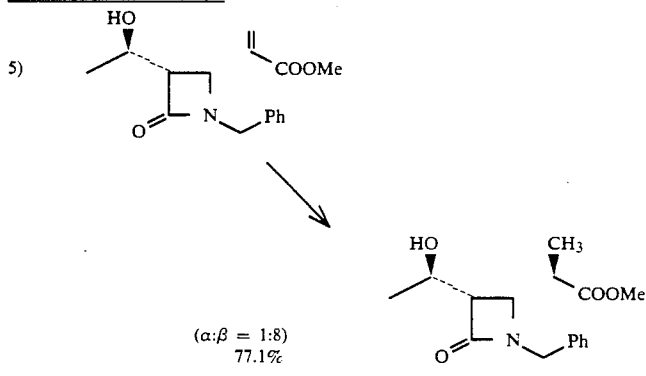

(α:β = 1:8)
77.1%

(3 steps)
(56%)

4

Tetrahedron Lett. 27, 2149 (1986)

[Isomerization]

6) 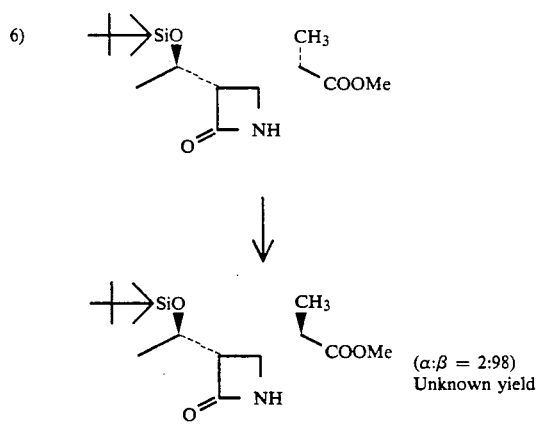

(α:β = 2:98)
Unknown yield

8th Symposium on Medicinal Chemistry, pp. 21 (1986)

These methods suffer from the defects that an increased number of steps are required; that the starting compounds are not easy to be produced; and that the yields are poor.

SUMMARY OF THE INVENTION

The present inventors found that the β-lactam compounds having a butynyl group at the 4-position which have not been described in the literature are employable as an important intermediate for 1β-methylcarbapenem compounds and discovered the simple and convenient methods for producing the above-described β-lactam compounds, which lead us to the establishment of this invention.

This invention is directed to:

β-Lactam compounds of the following general formula:

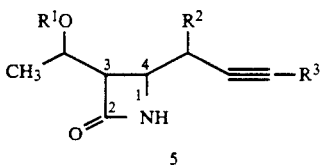

5

(wherein $OR^1$ is a protected or unprotected hydroxyl group; $R^2$ is a $C_1$ to $C_7$ alkyl or aryl group; $R^3$ is hydrogen or a tri-substituted silyl group), and a process for producing β-lactam compounds of the following general formula:

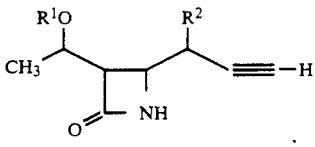

5

(wherein $OR^1$ and $R^2$ are as defined hereinbefore), characterized in that said process comprises reacting an azetidinone of the following general formula:

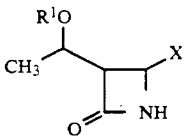

6

(wherein $OR^1$ is as defined hereinbefore; X is an electronegative group which is removable through reaction) with a stannylallene represented by the general formula $R^2$—CH=C=CH—$SnR^7_3$ (7) (wherein $R^2$ is a $C_1$ to $C_7$ alkyl or aryl group; $R^7$ is a $C_1$ to $C_4$ alkyl or phenyl group) to give a β-lactam compound of the following general formula:

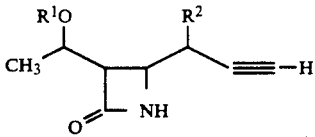

8

(wherein $OR^1$ and $R^2$ are as defined hereinbefore) and reacting said β-lactam compound with a base and an organosilyl halide represented by the general formula

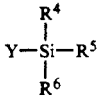

(wherein $R^4$, $R^5$ and $R^6$ are the same or different and each represents a $C_1$ to $C_4$ alkyl or aryl group; Y is a halogen), successively, to produce a β-lactam compound of the following general formula:

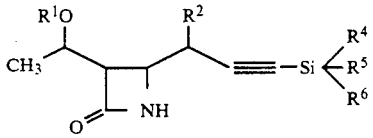

9 followed by subjecting said β-lactam compound to a removal reaction for the tri-substituted silyl group.

DETAILED DESCRIPTION OF THE INVENTION

Referring particularly to the above-described formula, in cases where $OR^1$ is a protected hydroxyl group, examples of the protective group represented by $R^1$ include substituted silyl groups, such as tert-butyldimethylsilyl, tert-butyldiphenylsilyl and triisopropylsilyl groups, and carboxylic acid ester groups, such as p-nitrobenzyloxycarbonyl and p-methoxybenzyloxycarbonyl groups.

As the $C_1$ to $C_7$ alkyl group represented by $R^2$, there may be mentioned, for example, methyl, ethyl and heptyl groups, while examples of the aryl group represented by $R^2$ include phenyl group, etc.

The tri-substituted silyl group represented by $R^3$ is understood to denote the silyl group having its three hydrogens substituted by the same or different aliphatic or aromatic hydrocarbon radicals, respectively, with the said hydrocarbon radicals being preferably alkyl or aryl groups. More preferred examples can be represented by the formula

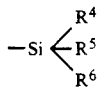

(wherein $R^4$, $R^5$ and $R^6$ are the same or different and each represents a $C_1$ to $C_4$ alkyl or aryl group). Desirable specific examples of $R^3$ include trimethylsilyl, triethylsilyl, triisopropylsilyl, tert-butyldimethylsilyl and dimethylphenylsilyl groups.

As the $C_1$ to $C_4$ alkyl group being represented individually by $R^4$, $R^5$ and $R^6$, there may be mentioned, for example, methyl, ethyl, propyl, isopropyl, butyl and tert-butyl groups, while examples of the aryl group include phenyl group, etc.

Examples of the $C_1$ to $C_4$ alkyl group represented by $R^7$ include methyl, ethyl, propyl and butyl groups, while as the aryl group, there may be mentioned phenyl group and the like.

The β-lactam compounds (5) of this invention are novel and can offer the advantages that the compounds have at the 4-position a butynyl group being convertible into various functional groups and also that the compounds can be produced in the form of β-lactam compounds possessing the desired configuration, for example, compounds (5') having the same configuration that the one of four consecutive asymmetric carbons possessed by the above-described 1β-methylcarbapenem compounds, when azetidinone compounds having the corresponding configuration are used as a starting compound in the production process according to this invention.

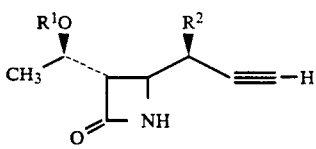

The compounds (9) and (5) of this invention can be produced by the following procedure:

The azetidinone compound (6) is reacted with stannyllallene (7) to produce the β-lactam compound (8).

This reaction is carried out in a halogenated hydrocarbon solvent, such as methylene chloride, chloroform and 1,2-dichloroethane, and a hydrocarbon solvent, such as n-hexane, benzene and toluene. Preferable is a halogenated hydrocarbon solvent.

The reaction is allowed to proceed in the presence of a Lewis acid. Preferred Lewis acids are boron trifluoride ethyl etherate [$BF_3 \cdot (C_2H_5)_2O$], trimethylsilyl trifluoromethanesulfonate [$(CH_3)_3 \cdot Si—OSO_2CF_3$] and tert-butyldimethylsilyl trifluoromethanesulfonate

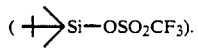

Usually, the reaction temperature is preferably in the range of $-10°$ C. to $60°$ C.

In this reaction step, for example, when the optically active azetidinone compound (6′) is used as a starting compound to undergo the reaction in the presence of $BF_3 \cdot (C_2H_5)_2O$ or $(CH_3)_3Si—OSO_2CF_3$ being utilized as a catalyst and in methylene chloride at room temperature, the β-lactam compound (8′) can be obtained almost quantitatively in the following ratios of the α- and β-forms in relation to the configuration of its methyl group:

In the case of $BF_3 \cdot (C_2H_5)_2O$ being used as a catalyst;

α:β = 4:1

In the case of $(CH_3)_3Si—OSO_2CF_3$ being utilized as a catalyst;

α:β = 1:1

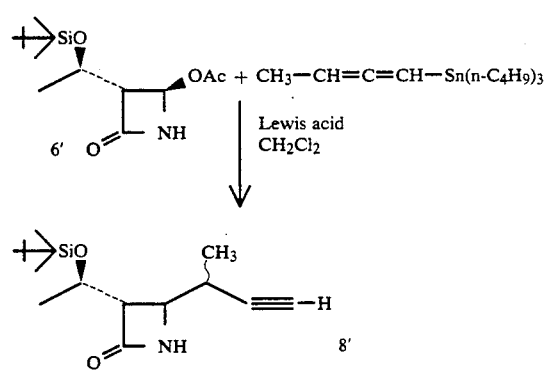

The compound (8) can also be obtained by allowing a metal compound represented by the formula $$R^2—\underset{\underset{M}{|}}{C}HC≡CH$$

(wherein $R^2$ is as defined hereinbefore; M is $—Mg \cdot X$ (X is halogen), Li, or a titanic acid ester or boric acid ester group, in place of stannylallene, to act on the compound (6). This reaction proceeds without addition of Lewis acid.

The β-lactam compound (8) as produced in the preceding step is reacted with a base and organosilyl halide, successively.

As the base, there are preferably employed lithium alkylamides, such a slithium diisopropylamide, and alkyl lithium, such as n-butyllithium-tetraethylenediamine, sec-butyllithium and tert-butyllithium.

The reaction is carried out in an anhydrous, inactive solvent, such as anhydrous tetrahydrofuran.

The resulting reaction product is subsequently reacted with an organosilyl halide represented by the formula

(wherein $R^4$, $R^5$ and $R^6$ are the same or different and each represents a $C_1$ to $C_4$ alkyl or aryl group; Y is a halogen) to produce the β-lactam compound (9).

Examples of the organosilyl halide include trimethylchlorosilane, triethylchlorosilane, tripropylchlorosilane, tert-butyldimethylchlorosilane and triphenylchlorosilane.

In the course of this reaction, the α-form of the compound (8) wherein the alkyl or aryl group represented by $R^2$ is involved in the configuration isomerizes to the β-form.

When the above-described compound (8′) having the α-form/β-form ratio of 1:1, being used as a starting compound in this reaction step, is reacted with 3.5 equivalents each of lithium diisopropylamide and trimethylchlorosilane successively in anhydrous tetrahydrofuran at $-78°$ C., for example, the α-form isomerizes to the β-form, resulting the high yield of the compound (9′) containing the α-form: β-form (1:13).

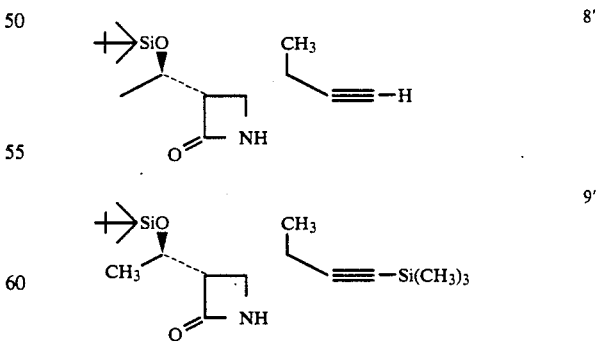

The compound (9) obtained thus can be derived to the compound (5) through a removal reaction for the tri-substituted silyl group.

This reaction can be carried out in the easier and quantitative manner by allowing silver nitrate and potassium cyanate successively to act on the compound (9) in a water-containing solvent or alternatively by allowing potassium fluoride to act on the compound in aqueous methanol.

By the above described procedure, for example, the compound (9') mentioned hereinbefore can be converted into the compound (5').

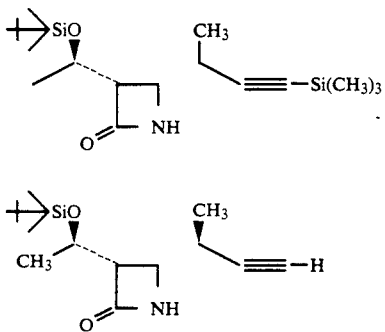

In the same manner as described above, the compound having a phenyl group instead of the methyl group in the substituent at 4-position of the azetidinone ring of the compound (5') can be obtained by employing 3-phenyl-1-tributylstannylallene in place of 3-methyl-1-tributyl-stannylallene.

The compounds of this invention can be derived to the important intermediate (4) as described hereinbefore, for example, through the reaction steps being illustrated below by the reaction formulas:

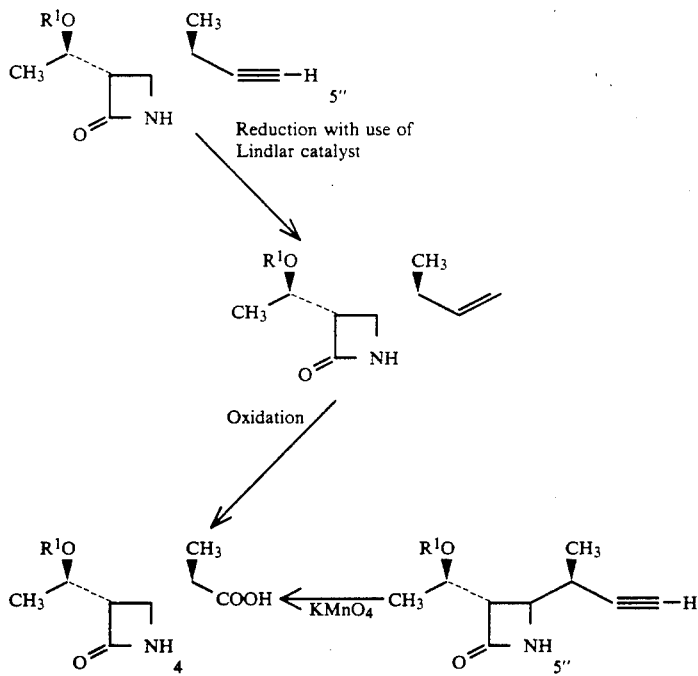

In addition, the compounds of this invention can be converted to optically active azetidinones being derivable into 1β-methylcarbapenem compounds other than those as described in the above.

The β-lactam compounds (5) having a butynyl group at the 4-position as obtained according to this invention can not only be easily derived to the azetidinone compounds (4), important intermediates for synthesizing for example 1β-methylcarbapenem (3), but also be produced in shortened steps in improved yields by starting from azetidinone compounds which are easily available or producible.

Below described are the examples and reference examples to illustrate more specifically this invention.

REFERENCE EXAMPLE 1

3-Methyl-1-tributylstannylallene
($CH_3$—CH=C=CHSnBu$_3$)

1-Bromo-3-methylallene (9.69 g) is added to 100 ml of anhydrous ether under a stream of nitrogen, followed by cooling to −78° C. n-Butyllithium (10 w/w % n-hexane solution) (46.7 ml) is added to the mixture under stirring over the period of 15 minutes, followed by stirring at the same temperature for 1 hour. After adding anhydrous tetrahydrofuran (20 ml), chlorotributylstannane (23.7 g) is added to the mixture over the period of 10 minutes, and the reaction mixture is allowed to warm up spontaneously to room temperature, followed by stirring at room temperature for 15 minutes. The reaction solution is poured into water, and extraction is performed with ether. The organic layer is washed with water and saturated aqueous sodium hydrochloride solution, successively, and dried over anhydrous magnesium sulfate. The solvent is removed under reduced pressure, and the residue is purified through silica gel column chromatography (n-hexane) to give 17.4 g of the objective compound.

IR (CHCl$_3$): 1,930 cm$^{-1}$
NMR (CDCl$_3$)δ: 0.7 to 2.0(27H,m), 1.65(3H,dd,J=4,7 Hz), 4.23(1H,dq,J=7,7 Hz), 5.05(1H,dq,J=4,7 Hz)

EXAMPLE 1

(3S,4R)-4-(1-Butyn-3-yl)-3-[(1R)-1-(tert-butyldimethyl-silyloxy)ethyl]-2-azetidinone (5''')

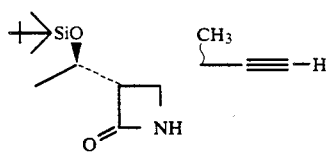

(3R,4R)-4-Acetoxy-3-[(1R)-1-(tert-butyldimethyl-silyloxy)ethyl]-2-azetidinone (653 mg) is added to 20 ml of anhydrous methylene chloride under a stream of nitrogen, followed by cooling with ice. After adding 3-methyl-1-tributylstannylallene (1.56 g), trimethylsilyl trifluoromethanesulfonate (0.35 ml) is added to the mixture, followed by stirring at the same temperature for 15 minutes and then at room temperature for 14 hours. The reaction solution is concentrated under reduced pressure, and the concentrate is admixed with ether. The mixture is washed with phosphoric acid buffer (pH 7) and admixed with saturated aqueous potassium fluoride solution, followed by stirring vigorously for 1 hour.

The resulting precipitate is filtered out, and the filtrate is dried over anhydrous magnesium sulfate, followed by removal of the solvent under reduced pressure. The residue is purified through silica gel column chromatography (n-hexane:ether=1:1) to give 626 mg of a 1:1 mixture of (3S,4R)-4-[1-butyn-3(R)-yl]-3-[(1R)-1-(tert-butyldimethylsilyloxy)ethyl]-2-azetidinone (α-methyl form) and (3S,4R)-4-[1-butyn-3(S)-yl]-3-[(1R)-1-(tert-butyldimethylsilyloxy)ethyl]-2-azetidinone (β-methyl form).

IR (CHCl$_3$): 3,420, 3,330, 1,755 cm$^{-1}$

NMR (90 MHz) (CDCl$_3$)δ: 0.08(6H,S), 0.88(9H,S), 1.24(6H,d, J=6 Hz), 2.12(1H,d,J=2.5 Hz), 2.59(1/2H,m,α-isomer), 2.70 (1/2H,m,β-isomer), 2.84(1/2H,m,α-isomer), 3.00(1/2H,m, β-isomer), 3.57(1/2H,dd,J=7.6,1.8 Hz,α-isomer), 3.67(1/2H, dd,J=6.4,2.0 Hz,β-isomer), 4.16-4.26(1H,m)

Exact mass spectrometry: as C$_{15}$H$_{27}$NO$_2$Si—C$_4$H$_9$.
Calcd.: 224.1108.
Found: 224.1108.

EXAMPLE 2

By following the same procedure as described in Example 1, 0.44 ml of boron trifluoride ethyl etherate (47% ether solution) is used in place of trimethylsilyl fluoromethanesulfonate to produce the compound (5''') (α-methyl form: β-methyl form=4:1). Yield of 569 mg.

EXAMPLE 3

(3S,4R)-4-[1-Butyn-3(S)-yl]-3-[(1R)-1-(tert-butyldimethylsilyloxy)ethyl]-2-azetidinone (5'''')

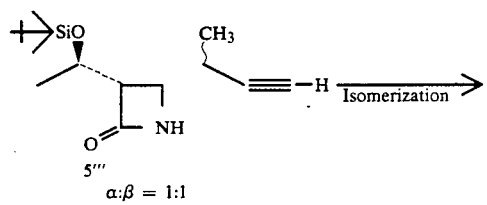

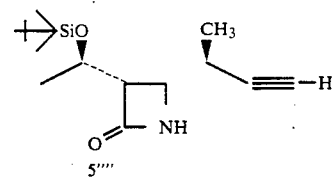

Diisopropylamine (0.34 ml) is added to anhydrous tetrahydrofuran (4.4 ml) under a stream of nitrogen, followed by cooling with ice. n-Butyllithium (10 w/w % n-hexane solution)(1.6 ml) is added to the solution, followed by stirring at the same temperature for 30 minutes. The solution is cooled to −78° C. and admixed with a solution in anhydrous tetrahydrofuran (4.4 ml) of the mixture (5''') (196 mg) of the α-methyl form and β-methyl form as obtained in Example 1, and the mixed solution is warmed up to −30° C. over the 1 hour period, then cooled down to −78° C. again and admixed with trimethylchlorosilane (0.31 ml). The reaction solution is allowed to warm up to room temperature spontaneously, and admixed with water and ethyl acetate, and the water layer separated is extracted with ethyl acetate. The combined organic layer is washed with water and saturated aqueous sodium chloride solution, successively and dried over anhydrous magnesium sulfate, followed by removal of the solvent under reduced pressure. The resulting residue is purified through silica gel column chromatography (n-hexane:ethyl acetate=4:1) to give 164 mg of (3S,4R)-4-[trimethylsilyl-1-butyn-3-(S)-yl]-3-[(1R)-1-(tert-butyldimethylsilyloxy)ethyl]-2-azetidinone.

IR (CHCl$_3$): 3,425, 2,160, 1,760

NMR (200 MHz) (CDCl$_3$)δ: 0.07(3H,S), 0.08(3H,S), 0.13 (9H,S), 0.88(9H,S), 1.23(6H,t,J=7 Hz), 2.66(1H,quint,J=7 Hz), 2.97(1H,bs), 3.63(1H,dd,J=2,7 Hz), 4.20 to 4.27(1H,m), 6.37(1H,bs).

Exact mass spectrometry: as C$_{18}$H$_{35}$NO$_2$Si$_2$—C$_4$H$_9$.
Calcd.: 296.1499.
Found: 296.1492.

The substance is dissolved in ethanol (1.4 ml), and the solution is cooled with ice and admixed gradually with a solution of silver nitrate (178 mg) in ethanol-water (1:3) (1.7 ml). After stirring for 15 minutes, 9M aqueous potassium cyanide solution (0.58 ml) is added to the solution, followed by stirring for 10 minutes and then at room temperature for 1 hour.

The reaction solution is admixed with ether (11 ml) and water (11 ml), and the aqueous layer is extracted with ether. The organic layer is washed with water and dried over anhydrous magnesium sulfate, and the solvent is removed under reduced pressure, followed by purification of the residue through silica gel column chromatography (n-hexane: ether=2:1) to give 127 mg of the desired compound.

IR (CHCl$_3$): 3,420, 3,300, 1,755 cm$^{-1}$

NMR (200 MHz) (CDCl$_3$)δ: 0.07(3H,S), 0.08(3H,S), 0.88(9H,S), 1.24(3H,d,J=6.8 Hz), 1.25(3H,d,J=6.2 Hz), 2.12(1H,d,J=2.4 Hz), 2.70(1H,d,of quint,J=2.4, 6.8 Hz), 2.99 to 3.02(1H,m), 3.67 (1H,dd,J=2,6.2 Hz), 4.23(1H,dq,J=6.2,4 Hz), 6.00(1H,brs).

Exact mass spectrometry: as C$_{15}$H$_{27}$NO$_2$Si—C$_4$H$_9$.
Calcd.: 224.1108.
Found: 224.1108.

EXAMPLE 4

3-Phenyl-1-trifutylstannylallene

1-Phenyl-2-propyn-1-ol (1.32 g) is converted to mesylate in accordance with the conventional method while using methanesulfonyl chloride and triethylamine. Tributylstannyllithium as produced by acting on bis-tributylstannane (5.8 g) and an equimolar amount of n-butyllithium (10 w/v % n-hexane solution) (6.4 ml) in tetrahydrofuran (10 ml) is added to a solution of cuprous bromide (1.43 g) and lithium bromide (0.87 g) in anhydrous tetrahydrofuran (30 ml) at $-60°$ C. to prepare an organic tin reagent (n-Bu$_3$SnLi), to which a solution of the above-described mesylate in anhydrous tetrahydrofuran (5 ml) is added at $-60°$ C., followed by stirring for 2 hours. The reaction solution is poured into saturated aqueous ammonium chloride solution, and extraction is performed with ether. The ether layer is dried over anhydrous magnesium sulfate, and the solvent is removed under reduced pressure. The resulting residue is purified by column chromatography on 6% aqueous alumina (n-hexane) to give 2.8 g of the objective compound.

IR (CHCl$_3$): 1,920, 1,595 cm$^{-1}$
NMR (90 MHz) (CDCl$_3$)$\delta$: 0.7 to 1.8(27H,m), 5.64(1H,d,J=7 Hz), 5.82(1H,d,J=7 Hz), 7.32 to 7.56 (5H,m).

EXAMPLE 5

(3S,4R)-4-(3-Phenyl-1-propyn-3-yl)-3-[(1R)-1-(tert-butyldimethylsilyloxy)ethyl]-2-azetidinone By following the same procedure as described in Example 2 except that 3-phenyl-1-tributylstannylallene (1.84 g) is used in place of 3-methyl-1-tributylstannylallene, there is obtained the objective compound. Yield of 640 mg.

IR (CHCl$_3$): 3,425, 3,320, 1,765 cm$^{-1}$
NMR (500 MHz) (CDCl$_3$)$\delta$: 0.04 (6H,S), 0.75(12/7H,d,J=6.7 Hz), 0,86(9H,S), 1.04(16/7H,d,J=6.7 Hz), 2.35(1H,t,J=2.4 Hz), 2.99 to 3.03(1H,m), 3.77(4/7H,t,J=1.8 Hz), 3.78 (3/7H,t,J=2.4 Hz), 3.84(4/7H,dd,J=6.7,2.2 Hz), 3.90(3/7H,dd, J=7.9,2.2 Hz), 4.11(4/7H,dq,J=4.3,6.7 Hz), 4.22(3/7H,dq,J=3.1,6.7 Hz), 7.34 to 7.41(5H,m).

EXAMPLE 6

(3S,4R)-4-[3-Phenyl-1-trimethylsilyl-1-propyn-3(R)-yl]-3-[(1R)-1-(tert-butyldimethylsilyloxy)ethyl]-2-azetidinone By following the first half of the same procedure as described in Example 3 except that 240 mg of the product as obtained in Example 5 is employed, with lithium diisopropylamide being used as a base, the isomerization reaction through silylation is carried out to produce 102 mg of the objective compound.

IR (CHCl$_3$): 3,410, 2,180, 1,760 cm$^{-1}$
NMR (90 MHz) (CDCl$_3$)$\delta$: 0.04(6H,S), 0.13(9H,S), 0.88(3H,d,J=6 Hz), 0.91(9H,S), 3.00 to 3.10(1H,m), 3.80 to 3.90(2H,m), 4.10 to 4.34(1H,m), 7.36(5H,S).

EXAMPLE 7

(3S,4R)-4-[3-Phenyl-1-propyn-3(R) -yl]-3-[(1R)-1-(tert-butyldimethylsilyloxy)ethyl]-2-azetidinone By following the last half of the same procedure as described in Example 3, 100 mg of the product as obtained in Example 6 is subjected to a removal reaction for silyl group to give 44 mg of the objective compound.

IR (CHCl$_3$): 3,425, 3,320, 1,765 cm$^{-1}$
NMR (500 MHz) (CDCl$_3$)$\delta$: 0.04(6H,S), 0.75(3H,d,J=6.7 Hz), 0.86(9H,S), 2.35(1H,d,J=2.4 Hz), 2.99 to 3.03(1H,m), 3.78 (1H,t,J=2.4 Hz), 3.90(1H,dd,J=7.9,2.2 Hz), 4.22(1H,dq,J=3.1, 6.7 Hz), 7.34 to 7.40(5H,m).

REFERENCE EXAMPLE 2

(3S,4R)-4-[1-Buten-3(S)-yl]-3-[(1R)-1-(tert-butyldimethylsilyloxy)ethyl]-2-azetidinone The 3-lactam compound (5''') (81 mg) as produced in Example 3 is dissolved in methanol (1 ml), and 5% Pd—BaSO$_4$ (1.6 mg) and quinoline (1.6 mg) are added to the solution, which is then allowed to absorb about 6.5 ml of hydrogen under atmospheric pressure at ambient temperature. The reaction solution is filtered, and the filtrate is admixed with ether and water to extract the aqueous layer with ether. The organic layer is washed with water and dried over anhydrous magnesium sulfate.

The solvent is removed under reduced pressure, and the residue is purified through silica gel column chromatography (n-hexane: ether=2:1) to give 73.4 mg of the objective compound.

IR (CHCl$_3$): 3,410, 1,750 cm$^{-1}$
NMR (200 MHz) (CDCl$_3$)$\delta$: 0.07(6H,S), 0.88(9H,S), 1.07 (3H,d,J=7 Hz). 1.17(3H,d,J=6 Hz), 2.33(1H,brq,J=7 Hz), 2.82 (1H,ddd,J=4.5,2.5,1 Hz), 3.52(1H,dd,J=8,2.5 Hz), 4.18(1H,dq, J=6,4.5 Hz), 4.96 to 5.22(2H,m), 5.60 to 6.00(2H,m).

Exact mass spectrometry: as $C_{11}H_{20}NO_2Si-C_4H_9$.
Calcd.: 226.126.
Found: 226.128.

We claim:

1. A process for producing a $\beta$-lactam compound of the following formula:

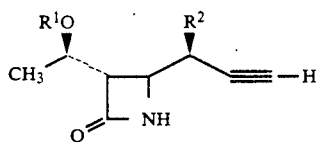

wherein OR$^1$ is a protected or unprotected hydroxyl group and R$^2$ is a C$_1$ to C$_7$ alkyl or aryl group in the $\beta$-form, which comprises reacting an azetidinone compound of the following formula:

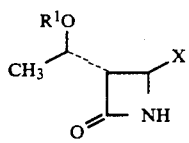

wherein OR$^1$ is the same as defined above and X is an electrogenative group removable through the reaction, with a stannylallene group of the formula R$^2$—CH=C=CH—SnR$^7_3$ wherein R$^2$ is the same as defined above and R$_7$ is a C$_1$ to C$_4$ alkyl group or a phenyl group, to give a $\beta$-lactam compound of the following formula:

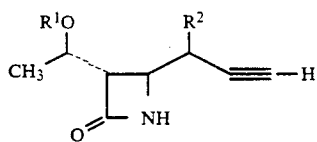

wherein $OR^1$ and $R^2$ are the same as defined above and $R^2$ is in α- and β-forms, and reacting said β-lactam compound with a lithium alkylamide or alkyllithium and an organosilyl halide of the formula:

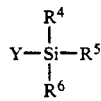

wherein $OR^1$ and $R^2$ are the same as defined above, and $R^4$, $R^5$ and $R^6$ are the same or different and each represents a $C_1$ to $C_4$ alkyl group or an aryl group, and Y is a halogen atom, successively, whereby the α-form of $R^2$ is isomerized to the β-form to produce a β-lactam compound of the following formula:

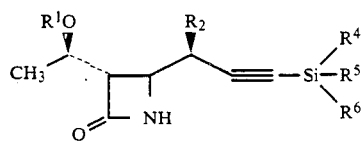

wherein $OR^1$ is a protected hydroxy group, and $R^2$, $R^4$, $R^5$ and $R^6$ are the same as defined above; and subjecting said β-lactam compound to a removal reaction of the group

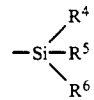

2. A method for isomerizing the α-form of a $R^2$ in a β-lactam compound of the formula:

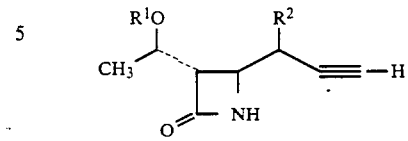

wherein $OR^1$ is a protected or unprotected hydroxyl group and $R^2$ is a $C_1$ to $C_7$ alkyl or aryl group, which comprises reacting said β-lactam compound with a lithium alkylamide or alkyllithium and an organosilyl halide of the formula:

wherein $R^4$, $R^5$ and $R^6$ are the same or different and each represents a $C_1$ to $C_4$ alkyl group or an aryl group, and Y is a halogen atom, successively, whereby the α-form of $R^2$ is isomerized to form the β-form, producing selectively a β-lactam compound of the formula:

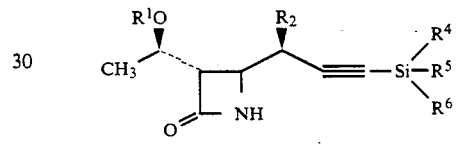

wherein $OR^1$, $R^2$, $R^4$, $R^5$ and $R^6$ are the same as defined above, and $R^2$ is in the β-form.

3. The process of claim 1, wherein $R^7$ is n-butyl and X is $CH_3COO$.

4. The process as claimed in claim 1, 3 or 2, wherein said lithium alkylamide is lithium diisopropylamide and said alkyllithium is selected from the group consisting of n-butyllithiumtetraethylenediamine, sec-butyllithium and tert-butyllithium.

* * * * *